DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 31, 1971

889 O.G. 1362

T889,001

PROCESS FOR PREPARING AROMATIC NITRILES FROM ALKYL AROMATIC HYDROCARBONS AND CATALYSTS THEREFOR

Howard S. Young, P.O. Box 511, Kingsport, Tenn. 37662

Continuation of application Ser. No. 688,352, Dec. 6, 1967. This application Sept. 19, 1969, Ser. No. 859,484

Int. Cl. B01j *11/06;* C07c *12/02*

U.S. Cl. 260—465C

No Drawing. 17 Pages Specification

Process for the ammoxidative conversion of alkyl-substituted aromatic hydrocarbons to the corresponding aromatic nitrile comprising contacting a mixture of vaporized hydrocarbon, ammonia and oxygen at a temperature of about 350° C. to 625° C. with a catalyst composition comprising oxidized molybdenum and at least one of oxidized niobium and oxidized tantalum and optionally oxidized arsenic. The aromatic hydrocarbons may include benzene and naphthalene substituted by at least one group represented by the formula $R_1R_2R_3C$— wherein $R_1$, $R_2$ and $R_3$ each represent a hydrogen atom or a lower alkyl group containing not more than 2 carbon atoms. An analysis of the components of the catalyst on a weight percent basis, when expressed as the theoretical oxides, is:

| | Percent |
|---|---|
| $MoO_3$ | 2–60 |
| $Nb_2O_5$ | 1–35 |
| $As_2O_3$ | 0–25 |
| Support | 0–90 |

or

| | |
|---|---|
| $MoO_3$ | 2–60 |
| $Ta_2O_5$ | 1–35 |
| $As_2O_3$ | 0–25 |
| Support | 0–90 |